United States Patent [19]

Whitley

[11] Patent Number: 5,399,170
[45] Date of Patent: Mar. 21, 1995

[54] SYRINGE

[75] Inventor: Kevin Whitley, Redfern, Australia

[73] Assignee: Western Medical Products Pty Limited, Sydney, Australia

[21] Appl. No.: 114,105

[22] Filed: Aug. 30, 1993

Related U.S. Application Data

[63] Continuation of Ser. No. 787,226, Nov. 4, 1991, abandoned.

[30] Foreign Application Priority Data

May 4, 1989 [AU] Australia ................. PJ4034

[51] Int. Cl.⁶ ............................................. A61M 5/32
[52] U.S. Cl. ......................... 604/198; 128/919; 604/110; 604/220; 604/263
[58] Field of Search ........ 128/919; 604/110, 195–198, 604/220, 221, 228, 229, 263, 240, 208–210, 192

[56] References Cited

U.S. PATENT DOCUMENTS

| | | |
|---|---|---|
| 2,626,604 | 1/1953 | Nadeau . |
| 3,306,290 | 2/1967 | Weltman . |
| 3,478,937 | 11/1969 | Solowey . |
| 3,890,971 | 6/1975 | Leeson et al. . |
| 4,026,287 | 5/1977 | Haller . |
| 4,391,272 | 7/1983 | Staempfli . |
| 4,507,117 | 3/1985 | Vining et al. . |
| 4,631,057 | 12/1986 | Mitchell . |
| 4,650,468 | 3/1987 | Jennings, Jr. ............ 604/110 |
| 4,702,738 | 10/1987 | Spencer . |
| 4,737,144 | 4/1988 | Choksi . |
| 4,747,829 | 5/1988 | Jacob et al. . |
| 4,747,830 | 5/1988 | Gloyer et al. . |
| 4,770,655 | 9/1988 | Haber et al. . |
| 4,770,655 | 9/1988 | Haber et al. ............ 604/110 |
| 4,781,684 | 11/1988 | Trenner ................. 604/110 |
| 4,801,295 | 1/1989 | Spencer . |
| 4,826,484 | 5/1989 | Haber et al. ............ 604/110 |
| 4,834,718 | 5/1989 | McDonald . |
| 4,846,796 | 7/1989 | Carrell et al. . |
| 4,871,355 | 10/1989 | Kikkawa . |
| 4,874,383 | 10/1979 | McNaughton .......... 604/263 |
| 4,878,899 | 11/1989 | Plouff ................... 604/110 |
| 4,906,231 | 3/1990 | Young .................. 604/110 |
| 4,908,023 | 3/1990 | Yuen .................... 604/110 |
| 4,917,679 | 4/1990 | Kronner . |
| 4,929,237 | 5/1990 | Medway . |
| 4,943,282 | 7/1990 | Page et al. ............ 604/198 |
| 4,961,730 | 10/1990 | Poncy . |
| 4,978,339 | 12/1990 | Labouze et al. . |
| 4,985,021 | 1/1991 | Straw et al. . |
| 4,994,045 | 2/1991 | Ranford . |
| 4,995,869 | 2/1991 | McCarthy . |
| 4,998,920 | 3/1991 | Johnson . |
| 4,998,924 | 3/1991 | Ranford . |
| 5,011,479 | 4/1990 | Le et al. . |
| 5,057,087 | 10/1991 | Harmon ................. 604/110 |
| 5,067,945 | 11/1991 | Ryan et al. ............ 604/263 |

FOREIGN PATENT DOCUMENTS

24163 3/1990 Philippines .

Primary Examiner—C. Fred Rosenbaum
Assistant Examiner—Ronald K. Stright, Jr.
Attorney, Agent, or Firm—Ladas & Parry

[57] ABSTRACT

A syringe (1) comprising a barrel (2) having an outer sheath (3) and an inner sheath (4). The outer sheath (3) has a nozzle (5) and the inner sheath also has a nozzle (6) which corresponds with and fits into, the nozzle (5). A needle (7) is attachable to the nozzle (6). A plunger (9) is located partly within the barrel (2) and is used to administer a drug. After the drug is administered the plunger (9) interlocks with the inner sheath (4) and as the plunger (9) is withdrawn, so too is the inner sheath (4). Hence the needle (7) is retracted to be within the outer sheath (3). After the needle (7) is retracted, the outer sheath (3) and inner sheath (4) are interlocked thus preventing the syringe (1) from being used again as well as locking the needle (7) in a safe retracted position within the outer sheath (3) thereby preventing "needle stick".

12 Claims, 9 Drawing Sheets

SYRINGE

This is a continuation application Ser. No. 07/787,226, filed on Nov. 4, 1991, now abandoned, which is a continuation-in-part of International Application PCT/AU90/00175, filed on May 1, 1990, and which designated the U.S.

The present invention relates to syringes and, in particular, to a syringe which is able to be disarmed after use.

BACKGROUND ART

It is the modern practice in medicine to dispose of used syringes and needles after only one operation. This practice has arisen due to possible contamination of the needle and syringe when administering to a patient.

Such a practice is strictly adhered to by medical practitioners and other ancillary staff in medical institutions. Therefore, the main problem in this regard in relation to hospitals and the like is not whether the syringes are used more than once but whether the syringes are disposed of correctly to avoid accidental skin puncture known as "needle stick". In this case responsible users of the syringes ensure that the syringes are correctly disposed of.

With the advent of increased use of intravenous drugs by drug addicts, there is an increasing incidence of repeated use of syringes by such users, and even several drug users using the same needle. This is unhygienic and tends to lead to the spread of infectious diseases, in particular hepatitis and AIDS.

It has been noted that education and free distribution of syringes and needles is one way of overcoming the possibility of the spread of such infectious diseases. The needle exchange programmes which have been initiated require that a syringe be returned before another one is issued. However, it has been acknowledged that these schemes are only successful up to a point, as it is possible for most conventional syringes to be used more than once, and used for more than one person. This ability to be re-used increases the risk of the spread of such diseases.

OBJECT OF THE INVENTION

It is the primary object of the present invention to provide a syringe which is able to be disarmed after use to thereby prevent "needle stick". It is a preferred feature of the present invention to provide such a syringe which is only able to be used once.

DISCLOSURE OF THE INVENTION

According to one aspect of the present invention there is disclosed a syringe to prevent "needle stick" after use, said syringe comprising an inner elongate sheath slidably located within an outer elongate sheath, said inner sheath having fixed at one end thereof needle means communicating with the interior of said inner sheath and extending through and beyond the corresponding end of said outer sheath when said inner sheath is closely adjacent said outer sheath corresponding end, a plunger slidably mounted in said inner sheath interior from the other end thereof and carrying a piston, said piston and said inner sheath interior defining a liquid drug receiving cavity of adjustable volume, a first two part locking means one part of which is carried by said plunger and the other part of which is carried by said inner sheath, said first two part locking means being arranged to inter-engage when said drug receiving cavity is substantially reduced to its minimum working volume by movement of said plunger towards said needle means to thereby cause said plunger and inner sheath to move together relative to said outer sheath, and a second two-part locking means one part of which is carried by said outer sheath and the other part of which is carried by said inner sheath, said second two part locking means being arranged to inter-engage when said inner sheath is moved relative to said outer sheath to draw said needle means into said outer sheath to thereby prevent said inner and outer sheaths sliding longitudinally relative to each other, and the length of said needle means and said outer sheath being selected to fully locate said needle means within said outer sheath when said second locking means is inter-engaged.

BRIEF DESCRIPTION OF THE DRAWINGS

One embodiment of the present invention will now be described with reference to the drawings in which.

BEST MODE OF CARRYING OUT THE INVENTION

Figure 1:
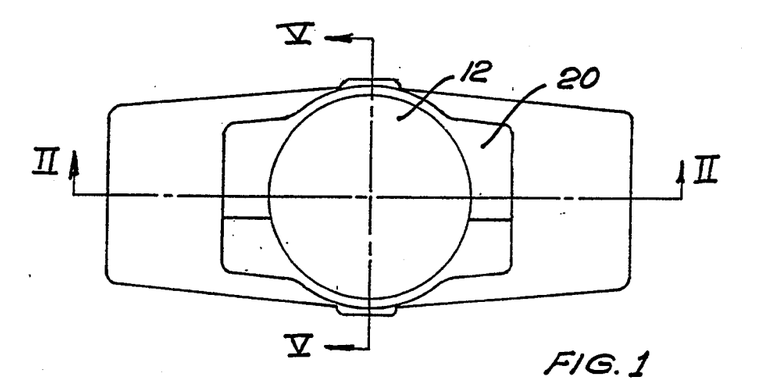
FIG. 1 is an end elevation of the syringe of the preferred embodiment.
Figure 2:
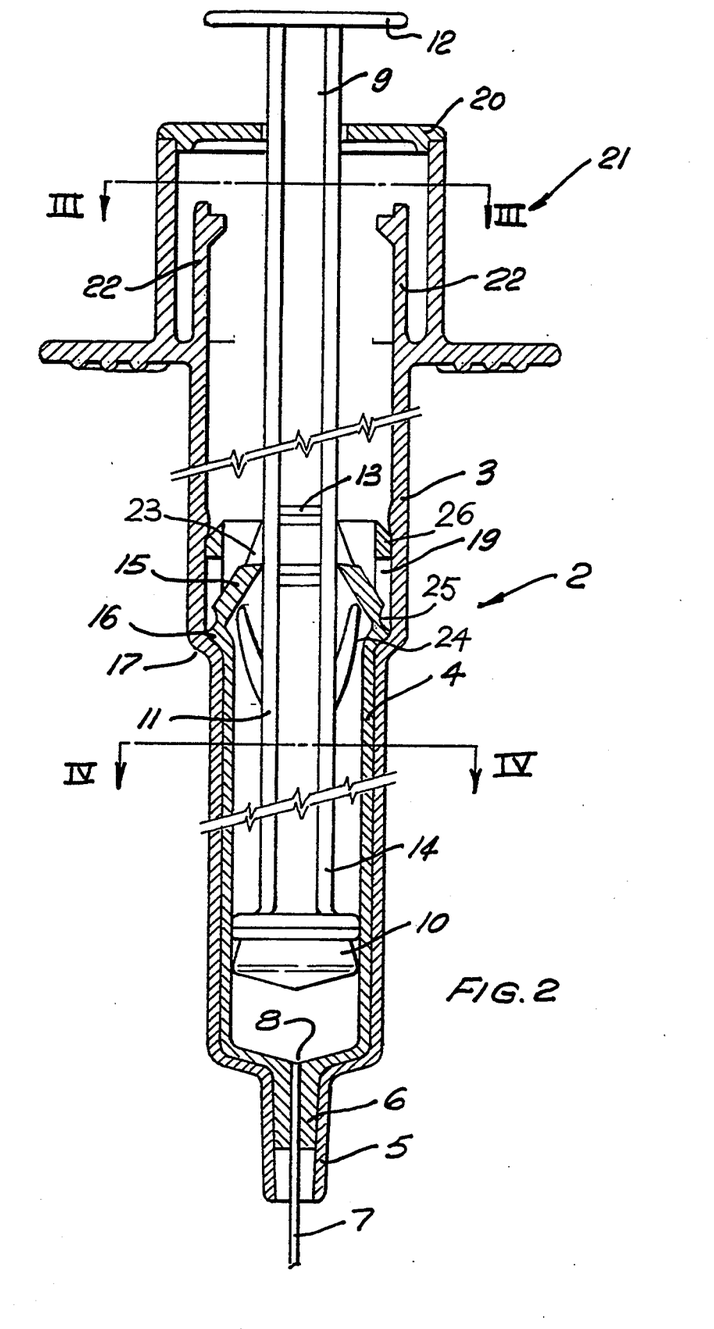
FIG. 2 is a longitudinal sectional view along the line A—A of FIG. 1.
Figure 7:
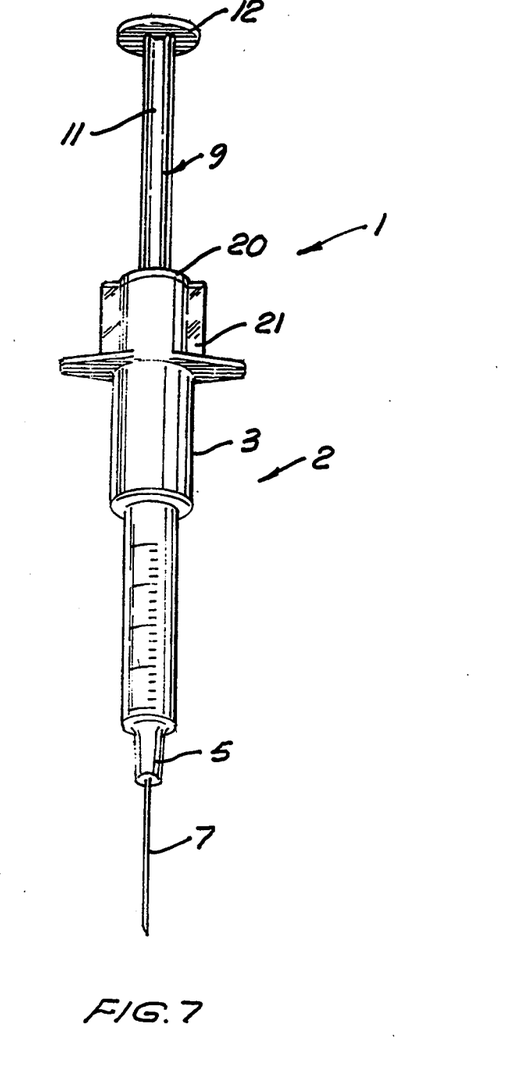
FIG. 7 is a perspective view of the syringe of the preferred embodiment.

As best seen in FIG. 7, the syringe 1 of the preferred embodiment has a barrel 2 having an outer sheath 3 and an inner sheath 4 (FIG. 2). The outer sheath 3 has a nozzle 5 and likewise the inner sheath 4 has a nozzle 6 the exterior of which is a friction fit within the interior of the nozzle 5. A needle 7 also is a friction fit within a central aperture 8 in the nozzle 6 of the inner sheath 4.

Figure 4:
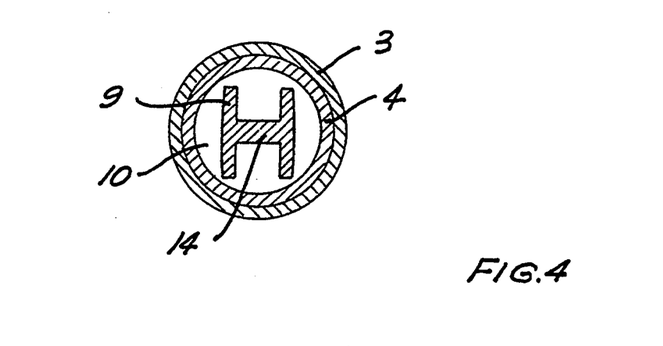
FIG. 4 is a transverse sectional view along the line IV—IV of FIG. 2.

A plunger 9 is generally similar to the plunger of a standard conventional syringe, as it includes a piston 10, a stem 11 and a base 12. However, a pair of locking ribs 13 (FIGS. 2 and 5) are located approximately midway on the stem 11 between two of the four flange portions 14 (FIG. 4) of the stem 11. A pair of safety locks 15 are integrally formed on the inner sheath 4. A pair of stops 23 on the plunger 9 are located adjacent the locking ribs 13 on the stem 11 and together with the locks 15 prevent accidental plunger lock before use. The safety locks 15 are connected to the inner sheath 4 by a thin piece of plastics material 25 which is able to be deformed.

The inner sheath 4 prior to use is as illustrated in FIG. 2 and fits snugly within the outer sheath 3. The inner sheath 4 has a shoulder 16 which fits within a corresponding shoulder 17 of the outer sheath 3. The location of the shoulders 16 and 17 is approximately midway along the barrel 2. The pair of safety locks 15 are seen in FIG. 2 to be resting against the pair of stops 23 so that the plunger 9 is not able to be moved in a downwards direction. Thus the safety locks 15 and stops 23 prevent accidental downwards movement of the plunger prior to use which could lock the mechanism of syringe 1 in a manner to be described hereafter.

A pair of resilient protruding fingers 24 are also located on the stem 11 of the plunger 9 and are arranged to interact with the safety locks 15 as the plunger 9 is withdrawn towards the needle 7 through a short distance.

Figure 3:
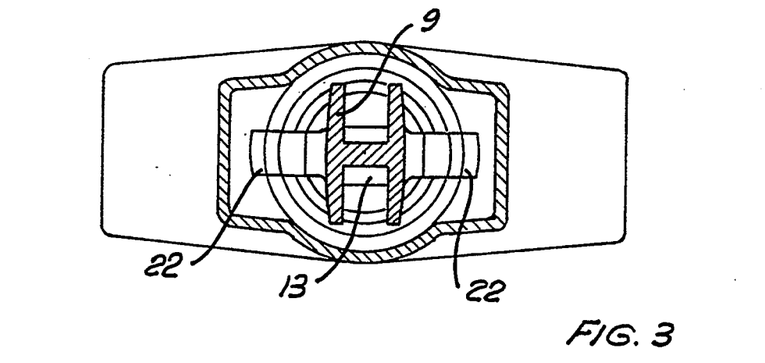
FIG. 3 is a transverse sectional view along the line III—III of FIG. 2.

As illustrated in FIG. 3, a pair of plunger locks 18 are located at the upper end 19 of the inner sheath 4, The plunger locks 18 are provided to interact with the locking ribs 13 after a single use of the syringe 1. Both the plunger locks 18 and the locking ribs 13 are made of resilient material.

A sealing cap 20 is located at the upper end 21 of the outer sheath 3 of the barrel 2, The sealing cap 20 is formed in two portions each integrally moulded with the barrel 3 of the syringe 1 and hinged thereto, After assembly of the syringe these two portions are welded to the barrel 3. This effectively seals the outer sheath 3.

A pair of locking hooks 22 (FIGS. 2 and 6) are located within the outer sheath 3 adjacent the sealing cap 20. The locking hooks 22 interact with corresponding protrusions 26 on the upper end 19 of the inner sheath 4 to prevent movement therebetween.

The syringe 1 is illustrated as ready for initial charging in FIG. 2. In this initial configuration, the inner sheath 4 and outer sheath 3 are in a position where the needle 7 is exposed, and the plunger 9 is ready to draw in a drug. First the plunger 9 is drawn in an upwards direction thus drawing in the liquid drug into the inner sheath 4 via the needle 7. This is a substantially conventional operation.

As the plunger 9 is drawn in the upwards direction, the fingers 24 deflect the safety locks 15 thus elastically deforming the thin piece of plastics material 25 which joins the safety locks 15 to the inner sheath 4. After this initial action, the safety locks 15 lie closer to the outer sheath 3 than the position illustrated in FIG. 2. Therefore the locks 15 are notable to prevent the downward movement of the plunger 9 by interaction with the stops 23 after the initial charging.

Due to the initial air gap between the piston 10 and the nozzle 6 as seen in FIG. 2, a small amount of air is mixed with the drug when drawn into the barrel 2. As is usual practice, this air is expelled prior to injection by moving the plunger 9 towards the needle 7 with the syringe held with the needle 7 uppermost.

Figure 5:
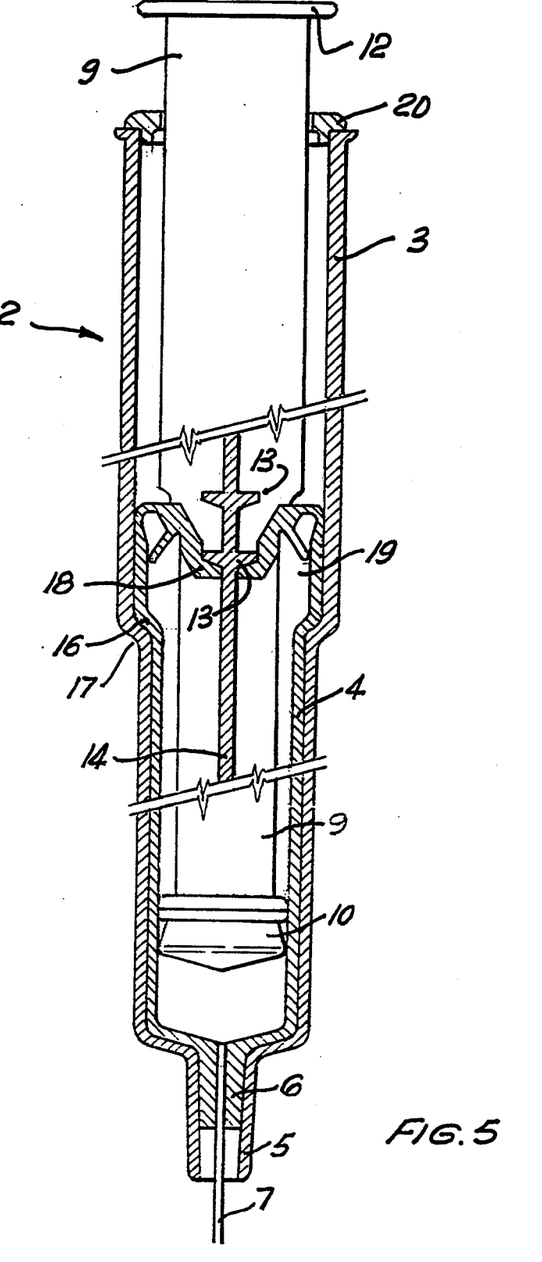
FIG. 5 is a longitudinal sectional view along the line V—V of FIG. 1.
Figure 6:
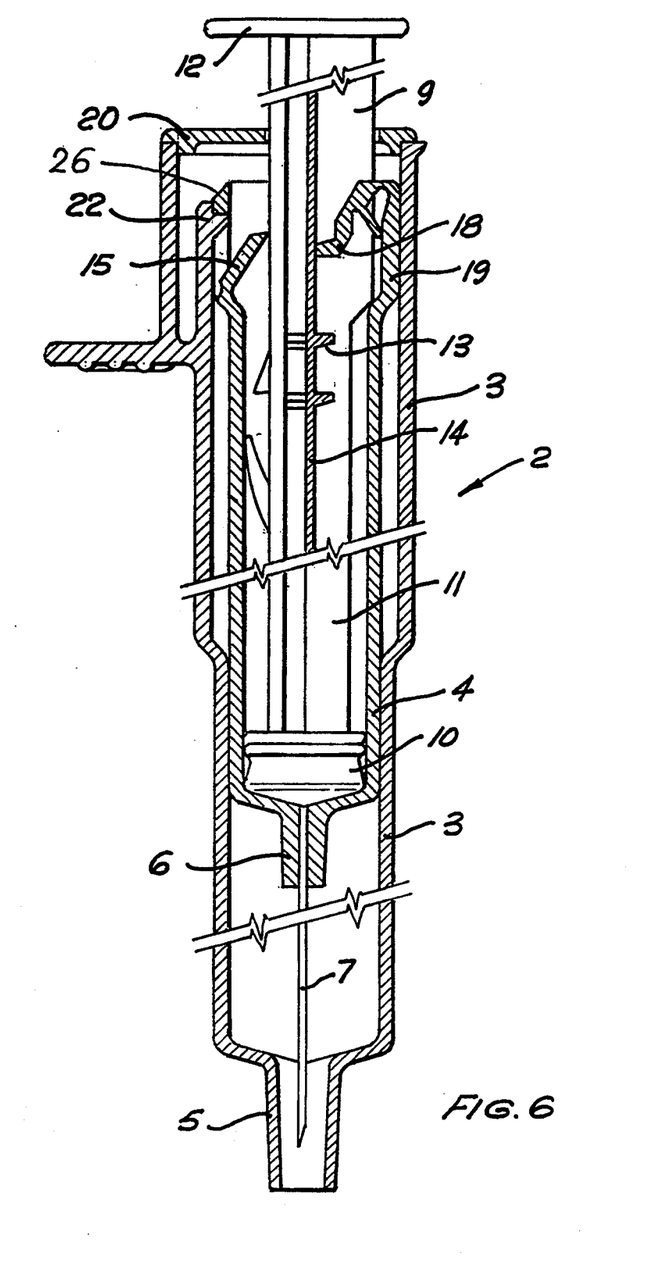
FIG. 6 is a longitudinal sectional view along the line II—II of FIG. 1.

Once the syringe 1 is thus readied for use, the plunger 9 is pressed in a downwards (with reference to the orientation of the syringe illustrated in FIGS. 2, 5 and 6) motion thus injecting the drug through the needle 7 by the piston 10 expelling the drug from the inner sheath 4. As illustrated in FIG. 5, shortly before the piston 10 reaches the end of its maximum distance of travel, the lower one of the two locking ribs 13 abuts the plunger locks 18. In this position the plunger 9 has reached what may be termed "the greed factor point". During unauthorized use of the syringe, particularly with initially gratifying illegal drugs, it is envisaged that the plunger 9 will be driven fully home so as to inject every possible drop of the drug.

This final motion of the plunger 9 moves the locking ribs 13 beyond the plunger locks 18. As a consequence, the inner sheath 4 and plunger 9 are locked together within the outer sheath 3 and an unobtrusive manner.

It will be appreciated that prior to engagement of the locking ribs 13 and plunger locks 18 the plunger 9 can be reciprocated within the inner sheath 4. This can be of assistance in expelling air from the drug or even re-filling the syringe if a greater volume of drug is to be administered than can be stored within the inner sheath 4.

Once the locking ribs 13 and plunger locks 18 have locked together, when the plunger 9 is pulled in a upward motion, the inner sheath 4 is also pulled upwardly. Thus the needle 7 is retracted into the interior of the outer sheath 3 as seen in FIG. 6. The syringe 1 is now able to be disposed of safely due to the covering of the needle 7 by the outer sheath 3. This helps to prevent "needle stick". The syringe 1 is also disarmed by the locking of the plunger 9 within the inner sheath 4 so that it cannot be used again.

However, it is desirable that the needle 7 be locked in the retracted position as illustrated in FIG. 6. Sufficient upward movement of the plunger 9, moves the protrusions 26 past the locking hooks 22 as seen in FIG. 6. This locks the outer sheath 3 and inner sheath 4 thus preventing any movement of the inner sheath 4 within the outer sheath 3. The syringe as well as being locked in a disarmed condition is also locked in a safe condition and is thus able to be disposed of safely.

Figure 8:
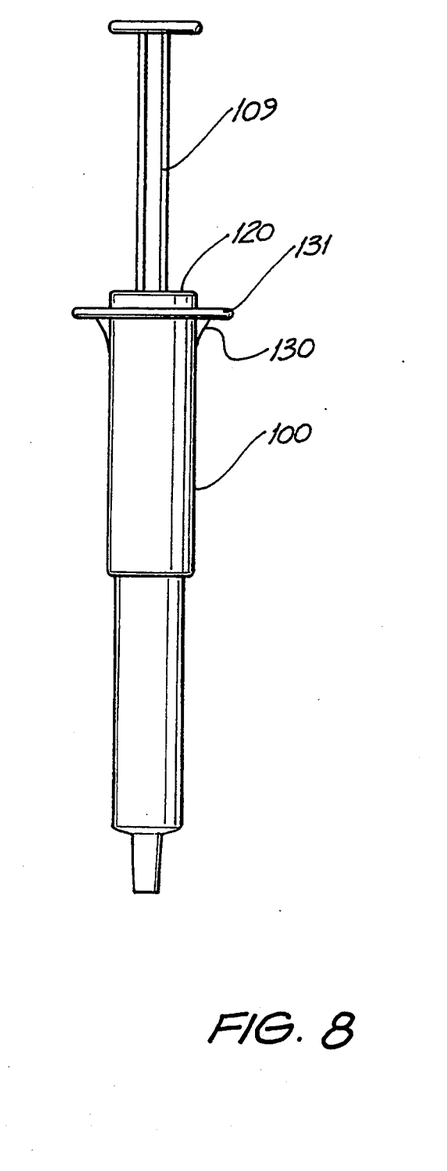
FIG. 8 is a side elevation of a syringe of a second embodiment.
Figure 9:
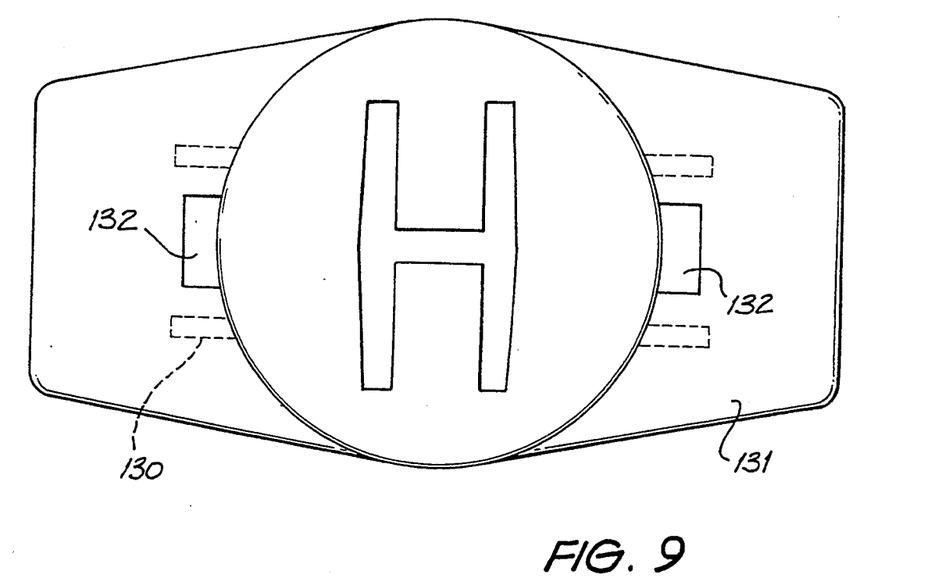
FIG. 9 is an end view similar to FIG. 1 but of the syringe of FIG. 8.
Figure 10:
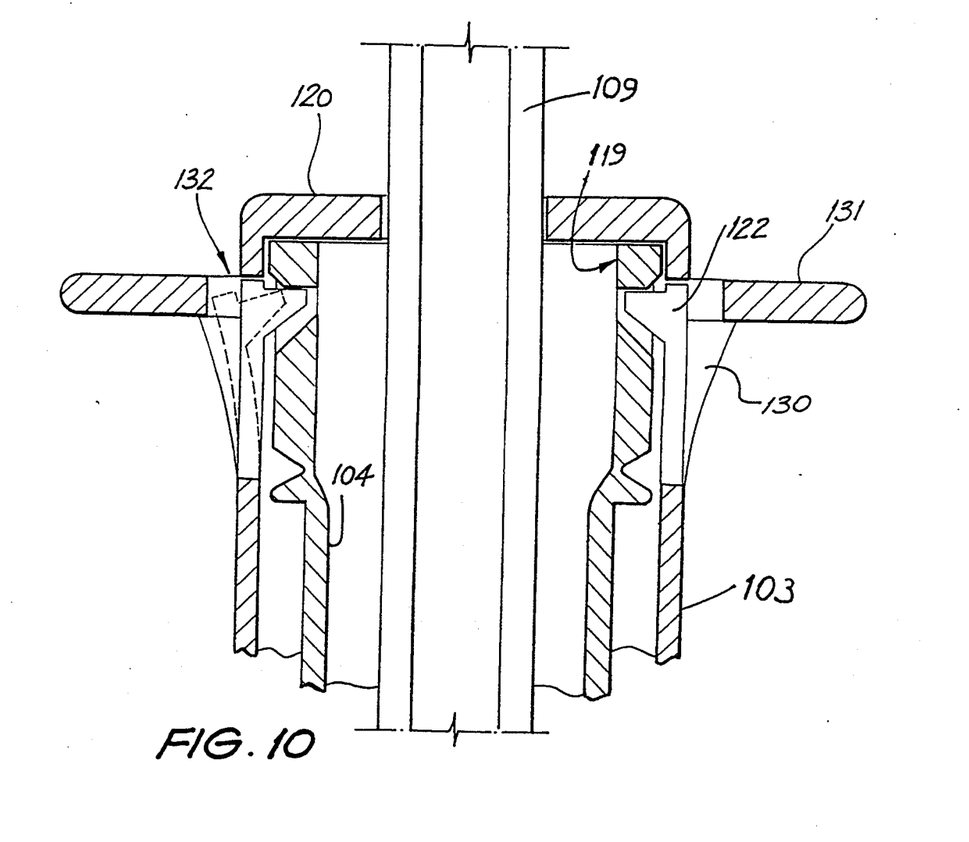
FIG. 10 is a longitudinal cross-sectional view similar to FIG. 2 but of the syringe of FIGS. 9 and 10.

Turning now to FIGS. 8–10, which illustrate a syringe 100 of a second embodiment, it will be seen that the thicker portion of the outer sheath 3 of the syringe 1 adjacent the cap 20 is missing. This comes about because of a revised arrangement for the locking hooks 22 of the syringe 1.

As seen in FIGS. 8–10, four webs 130 support the finger rests 131, the webs 130 and finger rests 131 being integrally moulded with the outer sheath 103. Located between each pair of webs 130 is an aperture 132 which extends through both the side wall of the sheath 103 and the corresponding finger rest 131. Centrally located within each aperture 132 is the corresponding one of a pair of locking hooks 122. As indicated by broken lines in FIG. 10, the locking hooks 122 are resiliently deflectable from their rest position.

As for the locking hooks 22 of the syringe 1, the locking hooks 122 of the syringe 100 engage the upper end 119 of the inner sheath 104. This holds the inner sheath 104 fully retracted within the syringe 100. A modified sealing cap 120, through which the plunger 109 passes, completes the arrangement.

Figure 11:
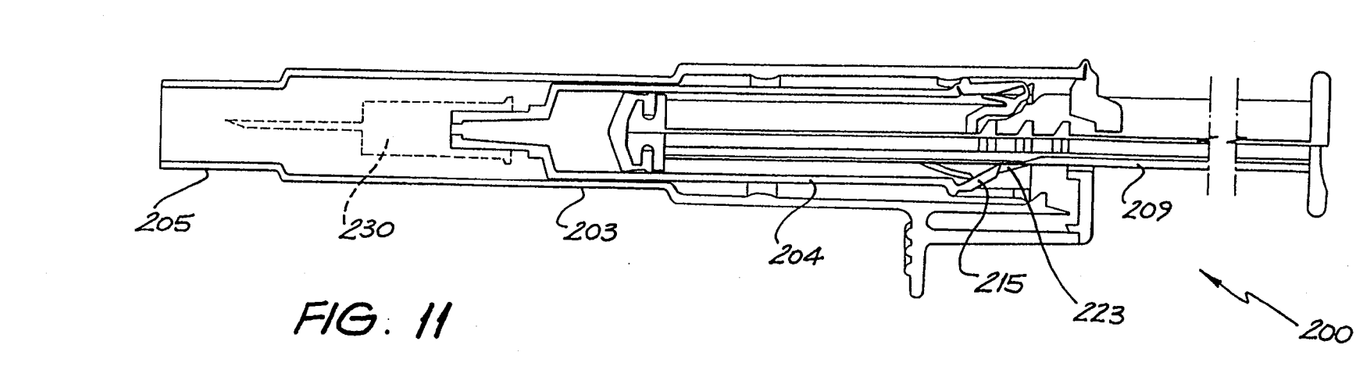
FIG. 11 is a view similar to FIG. 6 but showing a syringe of a third embodiment, in the initial assembled position.
Figure 12:
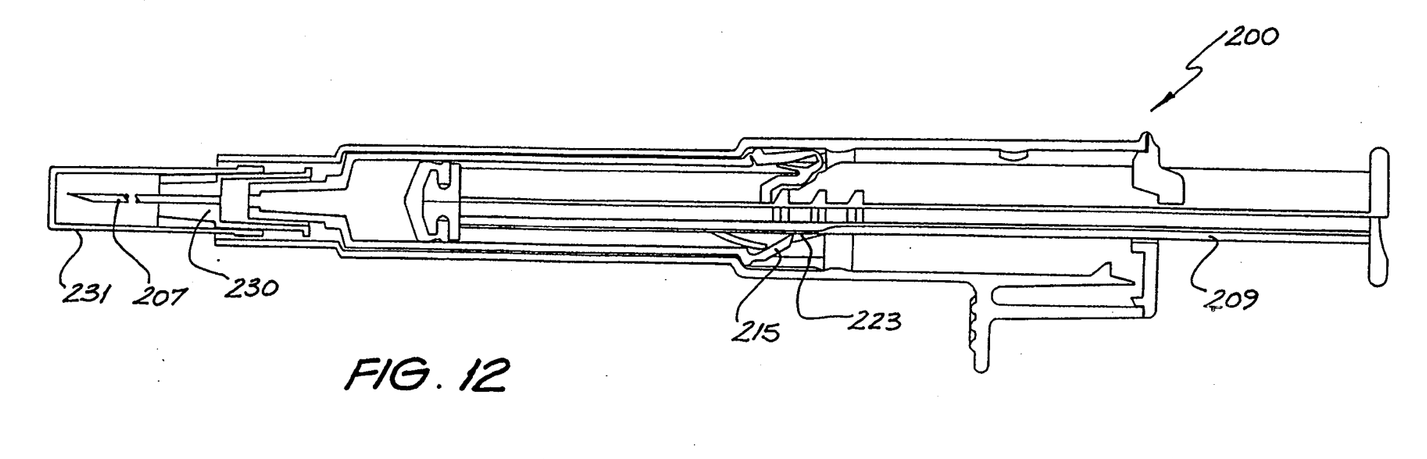
FIG. 12 is another view of the syringe of FIG. 11 but illustrating the fitting of a separate needle.

As seen in FIGS. 11 and 12, the syringe 200 of a third embodiment is provided with a modified nozzle 205 adapted to receive a LUER fitting 230 and needle 207 illustrated in broken lines in FIG. 11 and in full in FIG. 12. In both FIGS. 11 and 12, the stops 223 are engaged with the safety locks 215 in the manner illustrated in FIG. 2.

As seen in FIGS. 11 and 12, the internal diameter of the nozzle 205 is sufficient to receive the Luer fitting 230 and its associated needle cover 231. The operation of the syringe 200 is the same as that of the syringe 1. It will be appreciated that the inner sheath 204 can be retracted into, and locked within, the outer sheath 203 as before so as to render both the needle 207 safe and the plunger 209 immobilized.

Figures 13, 14:
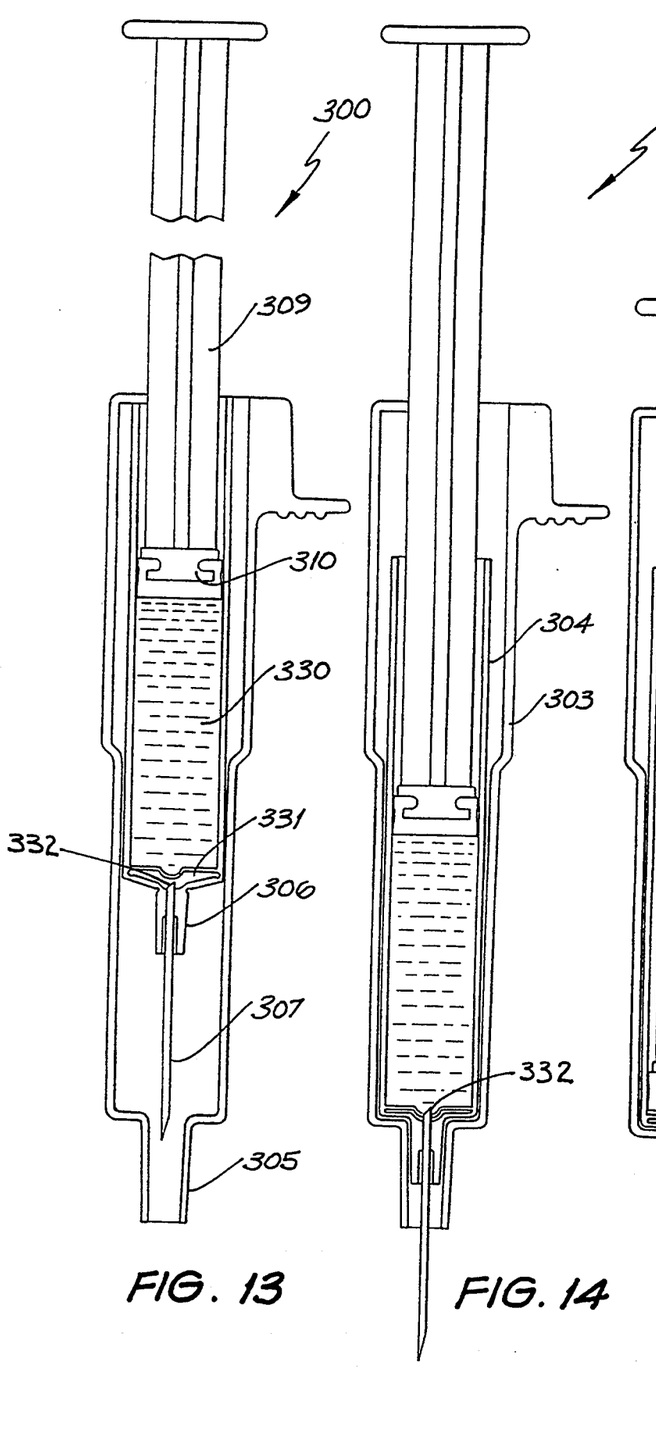
FIGS. 13–15 illustrate in longitudinal cross-section a pre-filled syringe of a fourth embodiment, the full details of inner and outer sheaths and the plunger being omitted.
Figure 15:
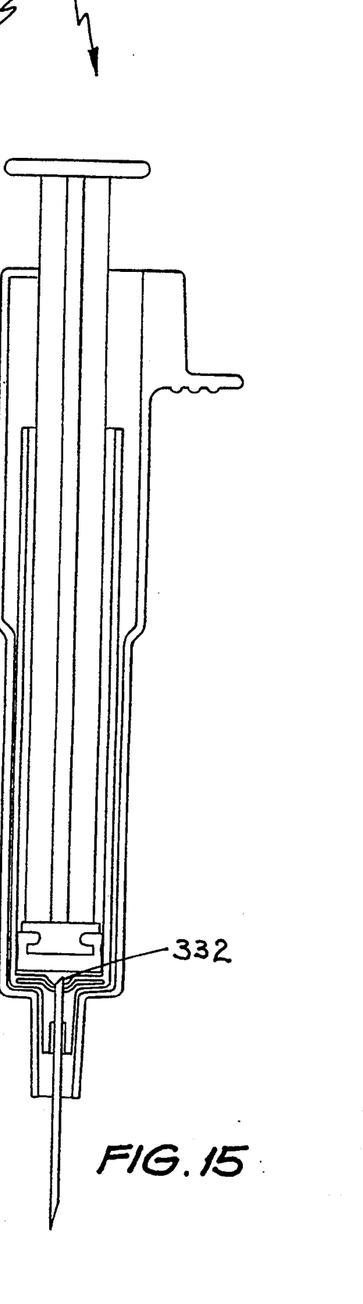

A syringe 300 of a fourth embodiment is illustrated in FIGS. 13-15. The syringe 300 is pre-filled with an injectable liquid 330 retained within the inner sheath 304 by the piston 310. The nozzle 306 of the inner sheath 304 is modified by the presence of a soft rubber wad 331 which covers the sharp inner end 332 of the needle 307. The wad 331 prevents the escape of, or contamination of, the liquid 330 via the needle 307.

In order to administer an injection, the plunger 309 is moved towards the nozzle 305. As before, firstly the inner sheath 304 is moved within the outer sheath 303 to engage the nozzles 305 and 306. Further movement of the plunger 309 forces the wad 331 onto and beyond the inner end 332 of the needle 307. As a consequence, the wad 331 is punctured and the injectable liquid can pass through the needle 307. This is illustrated in FIG. 14.

FIG. 15 illustrates the plunger 309 at the end of its stroke prior to withdrawal of the inner sheath 304 within the outer sheath 303. It will be appreciated by those skilled in the art that the interrelationship between the inner and outer sheaths 303,304 and the plunger 309 in FIGS. 13-15 is identical to that of the sheaths 3,4 and plunger 9 of FIGS. 1-7.

The foregoing describes only one embodiment of the present invention, and modifications obvious to those skilled in the art can be made thereto without departing from the scope of the present invention.

I claim:

1. A syringe to prevent "needle stick" after use, said syringe comprising an inner elongate sheath slidably located within an outer elongate sheath said inner sheath having at one end thereof needle means communicating with the interior of said inner sheath and passing through and beyond the corresponding end of said outer sheath when said one end of said inner sheath is closely adjacent said outer sheath corresponding end, a plunger slidably mounted in said inner sheath interior from the other end thereof and carrying a piston, said piston and said inner sheath interior defining a liquid drug receiving cavity of adjustable volume, a first two part locking means one part of which is carried by said plunger and the other part of which is carried by said inner sheath, said two parts of said first two part locking means being arranged to inter-engage with each other when said drug receiving cavity is substantially reduced to its minimum working volume by movement of said plunger towards said needle means to thereby cause said now connected plunger and inner sheath to move relative to said outer sheath, and a second two part locking means one part of which is carried by said outer sheath and the other part of which is carried by said inner sheath, said two parts of said second two part locking means being arranged to inter-engage with each other when said inner sheath is moved relative to said outer sheath to draw said needle means into said outer sheath to thereby prevent said inner and outer sheaths sliding longitudinally relative to each other, and the length of said needle means and said outer sheath being selected to fully locate said needle means within said outer sheath when said two parts of said second locking means are inter-engaged;

wherein a two-part deformable stop means is provided one part of which is deformable and located on said inner sheath and the other part of which is located on said plunger, said stop means parts inter-engaging to prevent motion of said plunger towards said needle means to an extent sufficient to inter-engage said first locking means, and said stop means being deformable by deflection means located on said plunger and movable past said one stop means part during initial movement of said plunger to fill said drug receiving cavity, after said deformation said one stop means part not being engageable with said other stop means part.

2. A syringe as claimed in claim 1, wherein said second locking means is not able to be released.

3. A syringe as claimed in claim 2, wherein said plunger extends through one end of said outer sheath through a cap means sealing said one end of said outer sheath, said cap means shielding said second locking means.

4. A syringe as claimed in claim 1, further comprising a stop abutment provided by said inner and outer sheaths which are shaped to limit the penetration of said inner sheath into said outer sheath.

5. A syringe as claimed in claim 4, wherein said stop abutment takes the form of substantially identical profiles on the exterior of said inner sheath and the interior of said outer sheath, said profiles providing a friction fit when abutted.

6. A syringe as claimed in claim 1, having a volume of injectable liquid in said drug receiving cavity.

7. A syringe as claimed in claim 6, wherein said needle means includes a sharpened interior end facing an impermeable wad.

8. A syringe as claimed in claim 1, wherein said two parts of said second locking means are positioned on said outer and inner sheaths to permit said inter-engagement thereof only when said needle means of said inner sheath is withdrawn into said outer sheath to substantially a maximum extent.

9. A syringe as claimed in claim 1, wherein said first locking means is not releasable to prevent said syringe being re-used after its initial use.

10. A syringe as claimed in claim 1, wherein said plunger is free to move back and forth within said inner sheath before said two parts of said first locking means are inter-engaged.

11. A syringe as claimed in claim 1, wherein said needle means comprises a nozzle shaped to releasably receive a detachable needle.

12. A syringe as claimed in claim 1, wherein said needle means comprises a needle secured to said one end of said inner sheath.

* * * * *